United States Patent
Whitfield et al.

(10) Patent No.: US 10,677,712 B2
(45) Date of Patent: Jun. 9, 2020

(54) HIGH-THROUGHPUT CORROSION TESTING PLATFORM

(71) Applicant: Massachusetts Institute of Technology, Cambridge, MA (US)

(72) Inventors: Matthew James Whitfield, Belmont, MA (US); Krystyn J. Van Vliet, Lexington, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 525 days.

(21) Appl. No.: 14/527,376

(22) Filed: Oct. 29, 2014

(65) Prior Publication Data
US 2015/0119286 A1   Apr. 30, 2015

Related U.S. Application Data

(60) Provisional application No. 61/896,870, filed on Oct. 29, 2013.

(51) Int. Cl.
| | | |
|---|---|---|
| *G01N 17/00* | (2006.01) | |
| *G01N 27/04* | (2006.01) | |
| *C12Q 1/02* | (2006.01) | |

(52) U.S. Cl.
CPC ......... *G01N 17/006* (2013.01); *G01N 17/002* (2013.01); *C12Q 1/02* (2013.01); *G01N 27/041* (2013.01)

(58) Field of Classification Search
CPC .. G01N 17/002; G01N 17/006; G01N 27/403; G01N 27/04; G01N 27/041; C12Q 1/02
USPC ............... 436/2, 6, 127, 136, 149, 164, 180; 422/82.01, 82.02, 400, 401, 407, 552, 53; 435/288.4, 288.7, 287.1, 29; 506/12, 39
See application file for complete search history.

(56) References Cited

U.S. PATENT DOCUMENTS

| | | | | |
|---|---|---|---|---|
| 5,405,513 | A * | 4/1995 | Lewis, II | G01N 17/00 204/404 |
| 6,365,034 | B1 * | 4/2002 | Spellane | G01N 17/02 204/404 |
| 7,589,539 | B2 * | 9/2009 | Butler | G01N 17/00 324/700 |
| 9,212,986 | B2 * | 12/2015 | Zhang | G01N 17/02 |
| 2007/0151942 | A1 * | 7/2007 | Dishongh | B01L 3/502707 216/13 |
| 2009/0158827 | A1 * | 6/2009 | Dermody | G01N 17/043 73/86 |
| 2011/0278024 | A1 * | 11/2011 | Ramachandran | C09K 8/594 166/402 |

FOREIGN PATENT DOCUMENTS

JP   2008-261652   * 10/2008

OTHER PUBLICATIONS

Whitfield et al. Corrosion Science, vol. 88, Aug. 2, 2014, pp. 481-486.*

* cited by examiner

*Primary Examiner* — Maureen Wallenhorst
(74) *Attorney, Agent, or Firm* — Steptoe & Johnson LLP

(57) ABSTRACT

A high-throughput corrosion testing mechanism was developed for metals in a variety of environments in controlled, multiplexed microenvironments. Many parallel experiments can be conducted with microbial and environmental variables independently manipulated to identify the key determinants of corrosion progression. The synthetic assay design enables subsequent surface characterization of select samples within the array. In as little as one day, diverse corrosive environments can be compared quantitatively.

50 Claims, 13 Drawing Sheets

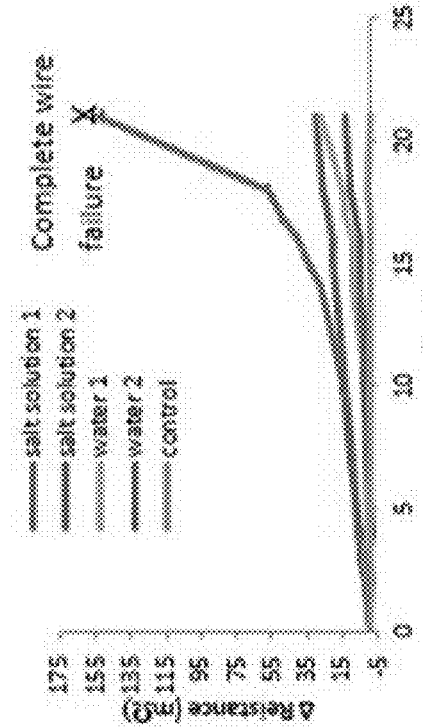
FIG. 7A
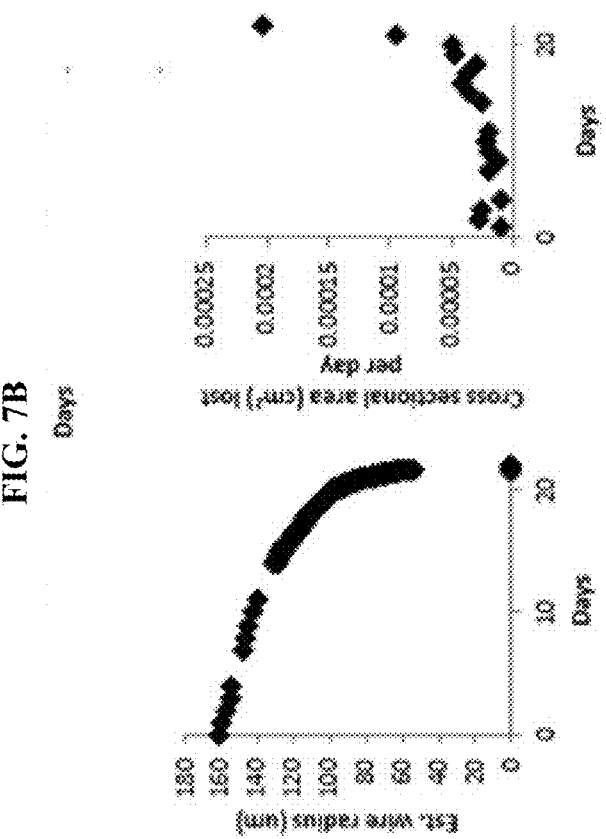
FIG. 7B
FIG. 7D
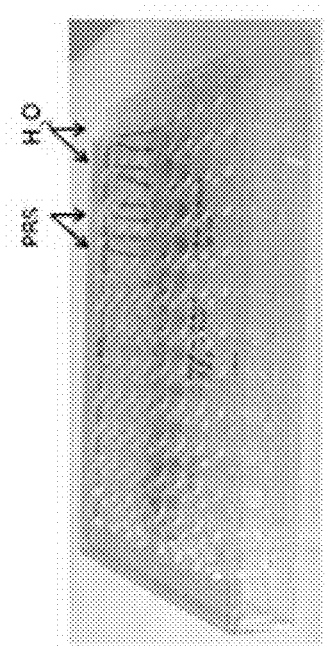
FIG. 7C
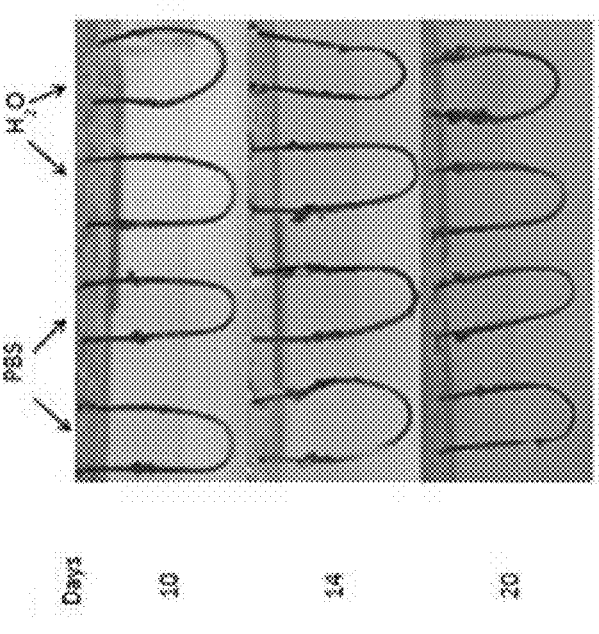

HIGH-THROUGHPUT CORROSION TESTING PLATFORM

CLAIM OF PRIORITY

This application claims the benefit of prior U.S. Provisional Application No. 61/896,870 filed on Oct. 29, 2013, which is incorporated by reference in its entirety.

TECHNICAL FIELD

The invention features systems and methods related to corrosion testing and microbial biofilm formation.

BACKGROUND

Microbiologically influenced corrosion (MIC) of metals is a major materials failure mode in a wide range of environments including water or fuel pipelines and medical devices. The corrosion process is highly complex, and its progression dependent on the particular environment and microbial species present. The mechanism by which MIC occurs and the environmental variables that predict the extent of corrosion are not well understood despite decades of research. New techniques that provide more sensitive and efficient ways to assess, monitor, and/or screen corrosion environments can aid in identifying susceptibility to complex corrosion mechanisms such as MIC.

SUMMARY

In general, a method and a system of assaying corrosion susceptibility of a sample can include providing a sample in a test cell, wherein the sample connects two electrical contact points in the test cell, and the test cell includes an environment, and measuring a property of the sample or the environment in the test cell. The property can be measured after incubating the sample in test cell for a defined period of time. The defined period of time can be less than a month, or a week, or a day. Alternatively, the property can be measured on a real-time basis while incubating the sample in the test cell.

The environment in the test cell can include a plurality of microbes. The environment can also include a solution and/or a gas. The gas can be oxygen. When the environment in the test cell includes a solution and/or a gas, the test cell can communicate with a source that is designed to replenish the solution and/or the gas. Alternatively, the test cell can be a tightly-sealed confined space. The confined space can be a well of a multiwell plate or a microfluidic channel.

The method of assaying corrosion susceptibility of a sample can include providing a plurality of test cells explained above and a plurality of samples, wherein each sample is incubated in a separate test cell, and measuring a property of each sample or each environment in the test cell. A plurality of test cells can be configured in a 96 well plate format.

To measure the property of the sample or the environment, one can measure the change of color of the sample or the environment, or the change of resistance of the sample, or the change of curvature of the sample.

The sample can be in the form of a wire. Specifically, the sample can be a wire loop or non-intersecting curved piece. A relatively small sample can be used for this method. For example, the sample can be less than 1 cm long. For example, sample can be a wire having a diameter of less than about 1 mm. The wire can form a loop, or non-intersecting curve, or arc with a radius of curvature of less than 1 cm.

Other aspects, embodiments, and features will be apparent from the following description, the drawings and the claims.

BRIEF DESCRIPTION OF THE DRAWINGS

FIGS. 7A and 7C are photographs depicting examples of aerobic corrosion testing under different conditions. FIG. 7B is a graph depicting the change of resistance as a function of time. FIG. 7D is a graph depicting reduction in wire thickness as a function of time.

FIG. 8A is a graph depicting the change of resistance as a function of time. FIG. 8B is a graph depicting the change of resistance as a function of a concentration of a salt solution.

DETAILED DESCRIPTION

Figure 1:
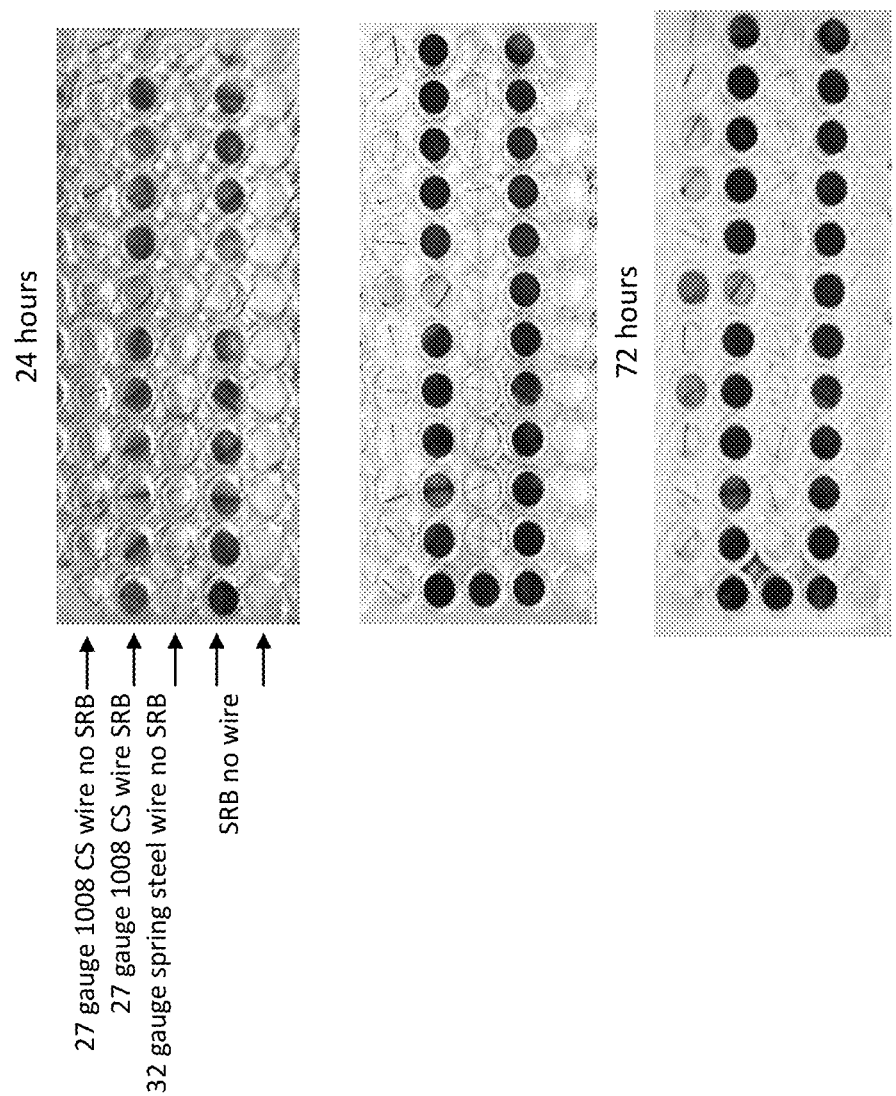
FIG. 1 is a photograph depicting one embodiment of a colorimetric assay for corrosion.

A high-throughput corrosion testing platform was developed to assay corrosion susceptibility of metals in a variety of physical environments. The concept focuses on detecting corrosion of small masses of metal, in the form of wires, in controlled microenvironments. Corrosion can be assessed by colorimetric means or by monitoring a change in electrical properties (e.g., resistance) of the metal. Results can be obtained over the course of hours, days, and weeks, which is rapid compared to traditional methods which often last months or longer. The conditions can be implemented in both aerobic and anaerobic environments and in both abiotic and biotic conditions. Corrosion of metals leads to material degradation, increased mechanical failure probability, and costly maintenance and repair in almost every environment. Significant research efforts and tremendous progress has been made in corrosion identification and mitigation. However, corrosion continues to plague many industries with estimated direct costs of over $276 billion every year in the US alone. See, Koch, G. H., et al., Corrosion cost and preventive strategies in the United States, 2002, Turner-Fairbank Highway Research Center, which is incorporated by reference in its entirety. One area where progress has lagged behind is areas where the presence of environmental microbes further confounds the issue. Microbial influenced corrosion (MIC) is a major ongoing problem in a wide range of environments such as oil and water pipelines and machinery, medical devices, and many other industries. Microbe-induced corrosion (MIC) and associated biofouling account for >25% of direct pipeline integrity and reliability costs exceeding $5 billion USD/year, and are implicated in several rapid, high-profile failures of buried pipeline. See, Abraham, G., Kain, V., Dey, G. K., MIC Failure of Type 316L Seawater Pipeline. Materials Performance, 2009. 48(1): p. 64-69, Yu, F. P., J. J. Dillon, and T. P. Henry, Identification And Control of Microbiologically Influenced Corrosion In a Power Plant. CORROSION 2010, 2010, Egan, M., Internal Corrosion Suspected as Cause of Alaskan Pipeline Leak. Materials Performance, 2011. 50(5): p. 14-23, and Al-Jaroudi, S., A. Ul-Hamid, and M. Al-Gahtani, Failure of crude oil pipeline due to microbiologically induced corrosion. Corrosion Engineering, Science and Technology, 2011. 46(4): p. 568-579, each of which is incorporated by reference in its entirety. However, the complex consortium of microbial species and the biofilms they produce have obviated mechanistic conclusions.

MIC can occur in both aerobic or anaerobic conditions, and is defined by no single characteristic trait other than corrosion in the presence of microbial species (bacteria) and their associated biofilms. Thus, MIC is considered biotic corrosion, and the terms "microbes" and "bacteria" are used interchangeably. As bacteria are ubiquitous in almost all environments (air, water, and organic fluids), the mere presence of bacteria found at sites of corrosion does not necessarily mean that the bacteria were a significant contributing factor in corrosion initiation or acceleration. MIC can occur in conjunction with other types of abiotic corrosion, further complicating attempts to identify the root cause of corrosion failure. Often, MIC is associated with surface pitting, which leads to more rapid corrosive failure than uniform corrosion. See, Bryant, R. D., Jansen, W., Boivin, J., Laishley, E. J., and Costerton, J. W. (1991). Effect of hydrogenase and mixed sulfate-reducing bacterial populations on the corrosion of steel. Appl. Environ. Microbiol., 57(10):2804-2809, Chamritski, I., Burns, G., Laycock, N., and Webster, B. (2004). Effect of iron-oxidizing bacteria on pitting of stainless steel. Corrosion, 60(07), Jan-Roblero, J., Romero, J., Amaya, M., and Le Borgne, S. (2004). Phylogenetic characterization of a corrosive consortium isolated from a sour gas pipeline. Appl. Microbiol. Biotechnol., 64(6):862-867, Miranda, E., Bethencourt, M., Botana, F., Cano, M., Sanchez-Amaya, J., Corzo, A., De Lomas, J., Fardeau, M., and Ollivier, B. (2006). Biocorrosion of carbon steel alloys by a hydrogenotrophic sulfate-reducing bacterium *desulfovibrio capillatus* isolated from a mexican oil field separator. Corros. Sci., 48(9):2417-2431, and Yuan, S. and Pehkonen, S. (2009). Afm study of microbialcolonization and its deleterious effect on 304 stainless steel by *Pseudomonas* ncimb 2021 and *desulfovibrio desulfuricans* in simulated seawater. Corros. Sci., 51(6):1372-1385, each of which is incorporated by reference in its entirety. Thus, even nonferrous metals that exhibit a naturally passivating layer at the surface (e.g., copper oxides and titanium oxides) exhibit MIC when metabolic byproducts of the microbes serve to chemically reduce and thus disrupt the passivating film under anaerobic conditions; this results in pitting corrosion at the metal-biofilm interface. See, Rao, T. (2012). Microbial Fouling and Corrosion: Fundamentals and Mechanisms, chapter 6, pages 95-126. Springer US, which is incorporated by reference in its entirety. As many surface characteristics including roughness, charge, and hydrophilicity can modulate bacterial adhesion, it is not yet clear whether bacteria initiate the pits or adhere preferentially to pre-existing pits. Although several studies have found evidence that microbes adhere preferentially to anodic metal regions such as welded joints, scratched edges, grain boundaries, or to previously corroded locations, a more recent study was not able to confirm these site-specific claim. See, Dexter, S. and Eashwar, M. (1999). Relation of bacterial settlement patterns to anodic activity on stainless steel weldments. Corrosion 99, Sreekumari, K., Nandakumar, K., and Kikuchi, Y. (2001). Bacterial attachment to stainless steel welds: significance of substratum microstructure. Biofouling, 17(4):303-316, Little, B., Ray, R., Wagner, P., Jones-Meehan, J., Lee, C., and Mansfeld, F. (1999). Spatial relationships between marine bacteria and localized corrosion on polymer coated steel. Biofouling, 13(4):301-321, and Sherar, B., Power, I., Keech, P., Mitlin, S., Southam, G., and Shoesmith, D. (2011). Characterizing the effect of carbon steel exposure in sulfide containing solutions to microbially induced corrosion. Corros. Sci., 53(3):955-960, each of which is incorporated by reference in its entirety. When many species of bacteria adhere and proliferate on a surface, they secrete a polysaccharide-rich matrix; a biofilm includes that extracellular polysaccharide matrix and the bacterial cells within. Attempts to spatially correlate localized corrosion with the overlying biofilm, e.g., using electrochemical mapping techniques, have failed due to the conductive nature of the biofilm itself. See, Dong, Z., Shi, W., Ruan, H., and Zhang, G. (2011). Heterogeneous corrosion of mild steel under srb-biofilm characterised by electrochemical mapping technique. Corros. Sci., 53(9):2978-2987, which is incorporated by reference in its entirety. Further, although pitting is a known signature of MIC, others have found no unique characteristics that distinguish the morphology of MIC pits from abiotic pits. See, Thomas, L. and Chung, Y. (1999). Comparison of mic pit morphology with chloride induced pits in types 304/3041/e308 stainless steel base metal/welds. Corrosion 99, which is incorporated by reference in its entirety.

At sites of suspected MIC, a so-called consortium of several bacterial species is always found—rather than a single species—though the number and types of bacteria in that consortium varies widely from location to location. Because the culture conditions of the majority of bacterial species are not well-established, determining the phylogenetic makeup is difficult. However, the application of molecular techniques now allow much more detailed analysis of extracts, quantifying the types and relative numbers of species. See, Amann, R. I., Ludwig, W., and Schleifer, K. H. (1995). Phylogenetic identification and in situ detection of individual microbial cells without cultivation. Microbiol. Rev., 59(1):143-69, which is incorporated by reference in its entirety. Several studies have performed detailed phylogenetic characterization of fluids from gas and oil pipelines and water outlet pipes at oil production facilities. See, Jan-Roblero, J., Romero, J., Amaya, M., and Le Borgne, S. (2004). Phylogenetic characterization of a corrosive consortium isolated from a sour gas pipeline. Appl. Microbiol. Biotechnol., 64(6):862-867, Rajasekar, A., Anandkumar, B., Maruthamuthu, S., Ting, Y., and Rahman, P. (2009). Characterization of corrosive bacterial consortia isolated from petroleum-product-transporting pipelines. Appl. Microbiol.

Biotechnol., 85(4):1175-1188, Maruthamuthu, S., Kumar, B. D., Ramachandran, S., Anandkumar, B., Palanichamy, S., Chandrasekaran, M., Subramanian, P., and Palaniswamy, N. (2011). Microbial corrosion in petroleum product transporting pipelines. Ind. Eng. Chem. Res., 50(13):8006-8015, and Larsen, J., Rasmussen, K., Pedersen, H., Sorensen, K., Lundgaard, T., and Skovhus, T. L. (2010). Consortia of MIC bacteria and archaea causing pitting corrosion in top side oil production facilities. Corrosion 2010, each of which is incorporated by reference in its entirety. The categories of bacteria typically directly linked to corrosion are sulfate-reducing bacteria (SRB), iron oxidizing bacteria, sulfur oxidizing bacteria, nitrate reducing bacteria (NRB), and methanogens. These bacteria may reduce the metal directly, produce corrosive metabolic byproducts, and/or produce biofilms that indirectly alter the local environment to promote corrosion. See, Rao, T. (2012). Microbial Fouling and Corrosion: Fundamentals and Mechanisms, chapter 6, pages 95-126. Springer US, which is incorporated by reference in its entirety.

As an example, while consortiums of microorganisms are typically involved in MIC in different contexts, sulfate reducing bacteria are considered a main culprit in anaerobic environments. SRB's reduce sulfates to sulfides as part of their metabolism. They have been hypothesized to contribute to the corrosion of iron surfaces through a number of mechanisms including cathodic depolarization, formation of corrosive hydrogen sulfide, production of hydrogenases, and establishment of differential anodic-cathodic regions due to heterogeneous biofilm formation. Most SRB are considered obligate anaerobes, meaning that the cells cannot metabolize and/or replicate in the presence of oxygen, although many species can temporarily tolerate low levels of oxygen. See, Johnson, M. S., Zhulin, I. B., Gapuzan, M., and Taylor, B. L. (1997). Oxygen-dependent growth of the obligate anaerobe *Desulfovibrio vulgaris* Hildenborough. J. Bacteriol., 179(17):5598-5601, which is incorporated by reference in its entirety. Furthermore, anaerobic conditions capable of supporting SRB growth can be created in overall aerobic environments, due to the microniches created within the bacterial biofilm/corrosion product layer. Although SRB are the most studied and well understood of the anaerobic corrosion inducing bacteria, MIC can occur in anaerobic conditions in the absence of SRB. See, Rajasekar, A., Anandkumar, B., Maruthamuthu, S., Ting, Y., and Rahman, P. (2009). Characterization of corrosive bacterial consortia isolated from petroleum-product-transporting pipelines. Appl. Microbiol. Biotechnol., 85(4):1175-1188, which is incorporated by reference in its entirety. Despite much research, there are still many unknowns as to the exact mechanisms by which they enhance corrosion and how to mitigate corrosive losses due to SRB's.

The highly complex nature of the corrosion processes themselves, along with added environmental variables, make teasing out contributions from the many variables difficult. Individually controlling for particular variables such as chemical composition of surrounding medium, gas concentrations, temperature, makeup of microbial species, the timing of the arrival of the species, flow rates, among others requires many separate experiments which are often not feasible using current techniques. Additionally, directed mutagenesis can provide insights into the mechanisms by with microbes enhance corrosion but again require 100s-1000s of separate experiments. New corrosive testing mechanisms need to be developed to allow the high-throughput testing required to answer many of the outstanding questions.

This has led to the development of several higher throughput techniques for measuring corrosion. Two recent articles review the state-of-the-art high-throughput techniques. See, Taylor, S., The investigation of corrosion phenomena with high throughput methods: a review. Corrosion Reviews, 2011. 29(3-4): p. 135-151, and Muster, T., et al., A review of high throughput and combinatorial electrochemistry. Electrochimica Acta, 2011. 56(27): p. 9679-9699, each of which is incorporated by reference in its entirety. Current techniques use either a single metal bulk substrate with areas controllably exposed to different microenvironments deposited metallic thin films in each microenvironment, or multiple electrode systems (2 or 3) within each microenvironment. See, for example, White, P., et al., A new high-throughput method for corrosion testing. Corrosion Science, 2012. 58: p. 327-331, Fleischauer, M., et al., Design and testing of a 64-channel combinatorial electrochemical cell. Journal of The Electrochemical Society, 2003. 150(11): p. A1465-A1469, Sun, T. X. and G. Jabbour, Combinatorial screening and optimization of luminescent materials and organic light-emitting devices. MRS bulletin, 2002. 27(04): p. 309-315, Chambers, B., S. Taylor, and M. Kendig, Rapid discovery of corrosion inhibitors and synergistic combinations using high-throughput screening methods. Corrosion, 2005. 61(5): p. 480-489, Muster, T., et al., A rapid screening multi-electrode method for the evaluation of corrosion inhibitors. Electrochimica Acta, 2009. 54(12): p. 3402-3411, Kallip, S., et al., A multi-electrode cell for high-throughput SVET screening of corrosion inhibitors. Corrosion Science, 2010. 52(9): p. 3146-3149, and Chambers, B. and S. Taylor, High-throughput assessment of inhibitor synergies on aluminum alloy 2024-T3 through measurement of surface copper enrichment. Corrosion, 2007. 63(3): p. 268-276, each of which is incorporated by reference in its entirety.

A method and a system of assaying corrosion susceptibility of a sample can include providing a sample in a test cell. The sample connects two electrical contact points in the test cell. The test cell includes an environment. The environment is selected to provide information about the sample, for example, its corrosion behavior in the presence of different materials or conditions. A property of the sample or the environment is measured directly in the test cell. For example, the electrical, colorometric or other properties can be examined. The property can be measured after incubating the sample in test cell for a defined period of time, for example, a month, a week, or a specified number of days, for example, 1, 2 3, 4, 5 or 6 days. Alternatively, a property can be measured on a real-time basis while incubating the sample in the test cell.

The environment in the test cell can include a plurality of microbes. The environment can also include a solution and/or a gas. The gas can be oxygen. When the environment in the test cell includes a solution and/or a gas, the test cell can communicate with a source that is designed to replenish the solution and/or the gas. Alternatively, the test cell is a tightly-sealed confined space. The confined space can be a microfluidic channel.

The method of assaying corrosion susceptibility of a sample can include providing a plurality of test cells explained above and a plurality of samples, wherein each sample is incubated in a separate test cell, and measuring a property of each sample or each environment in the test cell. A plurality of test cells can be configured in a 96 well plate format.

To measure the property of the sample or the environment, one can measure the change of color of the sample or the environment, or the change of resistance of the sample, or the change of curvature of the sample.

The sample can be in the form of a wire. Specifically, the sample can be a wire loop or non-intersecting curved piece. A relatively small sample can be used for this method. For example, the sample can be less than 1 cm long. For example, sample can be a wire having a diameter of less than about 1 mm. The wire can form a loop, or non-intersecting curve, or arc with a radius of curvature of less than 1 cm.

The use of wire in corrosion assays provides several advantages over standard techniques that make it amenable to rapid, high-throughput corrosion techniques. First, wire can be easily adapted to almost any conformation allowing use in confined environments such a 96 well plates and microfluidic channels. Also, wire provides high surface area in contact with the environment, which leads to a fast corrosion process. The small scale of the studies allows rapid assessment of corrosion when compared to traditional studies which are conducted on large pieces of steel over the course of months and analyzed with low-throughput methods such as AFM or SEM. In addition, wires can be easily imaged, even providing a pseudo cross-sectional view of the corrosion process.

In addition to colorimetric changes that are readily visible as corrosion products are confined in small volumes, the wire allows tracking of corrosion via resistance changes as the wire undergoes corrosion. Resistance-based probes have been validated as an effective means to measure corrosion albeit at a much larger scale with only a few samples. See, Royer, R. and R. Unz, Use of electrical resistance probes for studying microbiologically influenced corrosion. Corrosion, 2002. 58(10), and Li, S., et al., Application of steel thin film electrical resistance sensor for in situ corrosion monitoring. Sensors and Actuators B: Chemical, 2007. 120(2): p. 368-377, each of which is incorporated by reference in its entirety. While resistance measurements do not provide the detailed spatial information about corrosion that some other methods allow, they can be performed much more rapidly and do measure the overall corrosion rate of the sample which is typically the relevant measure when assessing corrosive ability. Conditions of interest identified with this method can then be further studied for other traits of interest.

During the assay, the sample of material is placed into analysis wells in a multi-well specimen. Each well can include a condition reagent that includes a composition created to test a particular environmental condition. The condition reagent in each cell can vary. Alternatively, or in addition, the nature of the sample in each cell can vary. The wells are then incubated in controlled conditions. Factors that can be controlled include temperature, time and atmosphere. The presence or alteration of a color in each well after incubation provides an indication of the effect the condition reagent has on the sample.

The condition reagent in the confined environment can include one or more components, for example, a salt component, an acid component, a base component, a surfactant component or a microbe component. The salinity can affect not only the corrosion itself but also the bacterial species present or the behavior of a given species. Salinity can be changed controllable through use of salts such as NaCl, KCl, etc or through mixtures obtained from the environment such as sea water, injection, or produced water. Any acid can be used in the confined environment. For example, hydrochloric acid or nitric acid can be used. Any base can be used in the confined environment, For example, sodium hydroxide can be used. Any bacteria including those known to promote corrosion, those known to passivate, and those with unknown function can be used. Also, pure populations of bacteria or well-controlled mixed populations, or unknown combinations of bacteria can be used. For example, pure sulfate reducing bacteria cultures (*Desulfovibrio vulgaris*) as corrosion promoting, *E. coli* as a non-corrosive control, and natural water sources as unclassified natural consortiums can be used.

The controlled conditions include specific time period, temperatures and atmospheres for testing. Examples of suitable time periods include seconds, minutes, hours or days. Examples of suitable temperatures are compatible with the device materials, which can include from 0° C. to 45° C., for example, around 30° C. Examples of suitable atmospheres can include air or anaerobic with specific mixtures such as 5% carbon dioxide, 5% hydrogen, balance nitrogen.

The sample materials can include any conductive material that can be produced or reshaped into a filament suitable for the wire resistance measurements. Examples of such materials include a wide variety of steels, copper, or carbon. Mixed material wire can also be used such as galvanized or otherwise treated wires.

The system is applicable to the simultaneous detection of multiple conditions and corrosion results. For example, under certain conditions, a first color can be produced upon incubation in the presence of a first condition reagent under a first condition, and a second color can be produced upon incubation in the presence of a second condition reagent under a second condition. Similarly, electrical properties of the sample can change. A range of colors or electrical properties can be developed that are indicative of corrosion behaviors for the materials under particular conditions. For instance, oxidative corrosion results in the production of ferrous oxides with orangish tint while anaerobic corrosion in the presence of sulfides results in black colored iron sulfides. The rate and manner of resistance change are of particular interest.

Colorimetric Assay of Corrosion and Oxygen Presence

A small piece of wire within a 96-well plate or other fluid-containing vessel can serve to determine if a given environment is corrosive. Small (~0.4-0.7 cm length) segments of wire were placed in individual wells of a 96-well plate. The wells contained a nutrient broth which was either inoculated with corrosive sulfate reducing bacteria (SRB) or kept sterile. The plate was sealed in a vacuum bag in order to approximate an anaerobic environment and placed in an incubator at 30° C. The results are shown in FIG. 1. Corrosion was observable by a color change of the medium when iron was removed from the wire and precipitated into the solution and was observed in the wells containing both wire and bacteria (rows 2 and 4) but not in wells containing only one of the two (rows 1, 3, and 5). This was demonstrated with both a 27 gauge 1008 carbon steel and 32 gauge spring steel wires. The time course of corrosion can also be observed as the color darkened over the course of three days. This metric did become saturated when a layer of iron precipitate settled onto the bottom surface of the well.

This embodiment also demonstrates the capability of this system to be used as a contamination control, as seen from the first well in row 3 where the contents of an adjacent well contaminated the well when over-filled. Additionally, because these experiments were conducted in semi-anaerobic conditions, some oxygen was still present and manifests as the yellow and brown coloring (corrosion products) in the first row. This indicates the ability to colorimetrically distinguish between the two types of corrosion, as well as monitor for the presence of oxygen.

Figure 2:
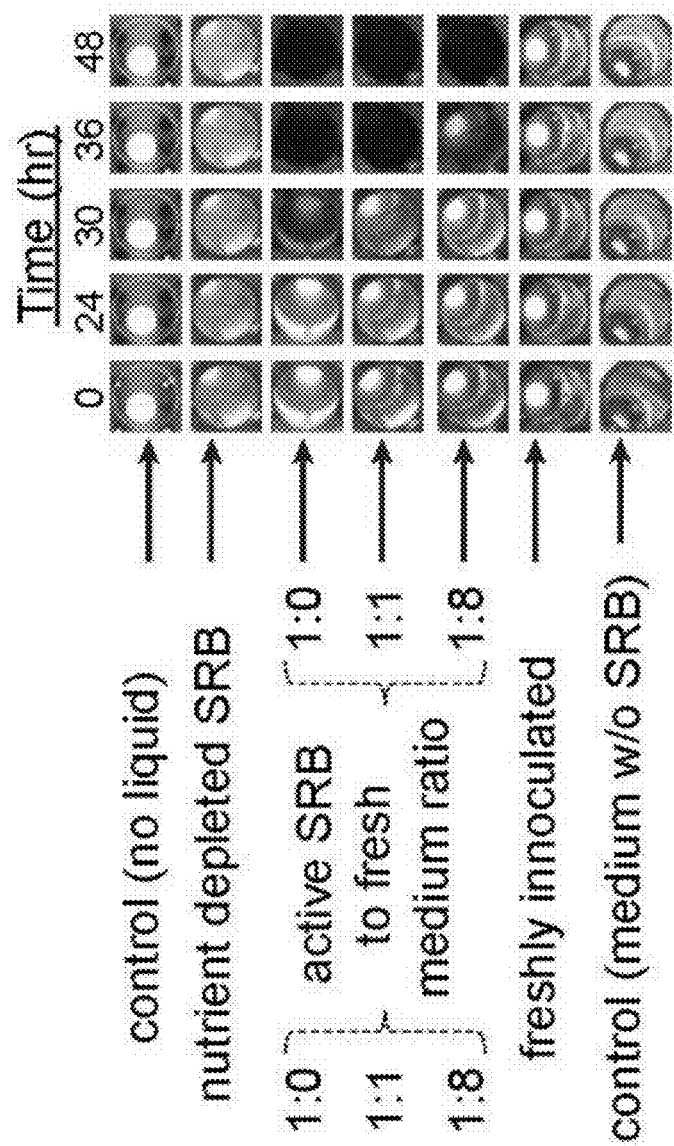
FIG. 2 is a photograph depicting another embodiment of a colorimetric assay for corrosion.
Figure 3:
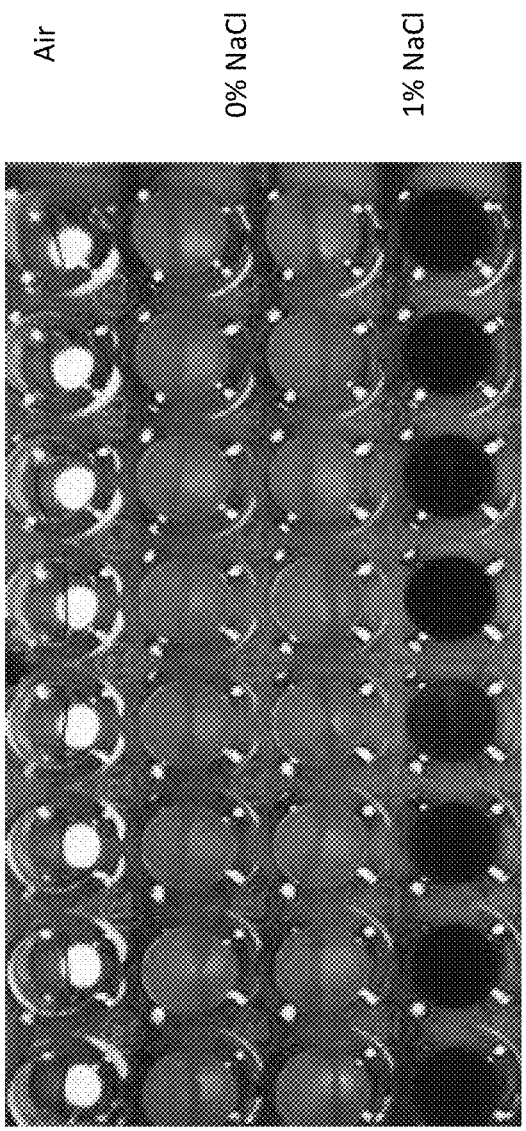
FIG. 3 is a photograph depicting a third embodiment of a colorimetric assay for corrosion.

In another embodiment, u-shaped wire loops were suspended within each well of a 96-well plate and placed in conditions containing SRB and varying amounts of bacterial nutrients. FIG. 2 shows the color change over time for representative wells at the different conditions. The characteristic black color of iron sulfides in anaerobic conditions was observed sooner for environments with a high concentration of bacteria provided with sufficient nutrients. In another embodiment, u-shaped wire loops were suspended within each well of a 96-well plate and placed in conditions containing various concentrations of sodium chloride. FIG. 3 shows the color change after 24 hours for conditions with no liquid (air), purified water, and 1% sodium chloride (w/v). Each row is 8 repeats of the same condition. Color changes are consistent and the presence of salt can easily be identified.

Resistance Measurement Assay of Corrosion Rate and Extent

Figure 4:
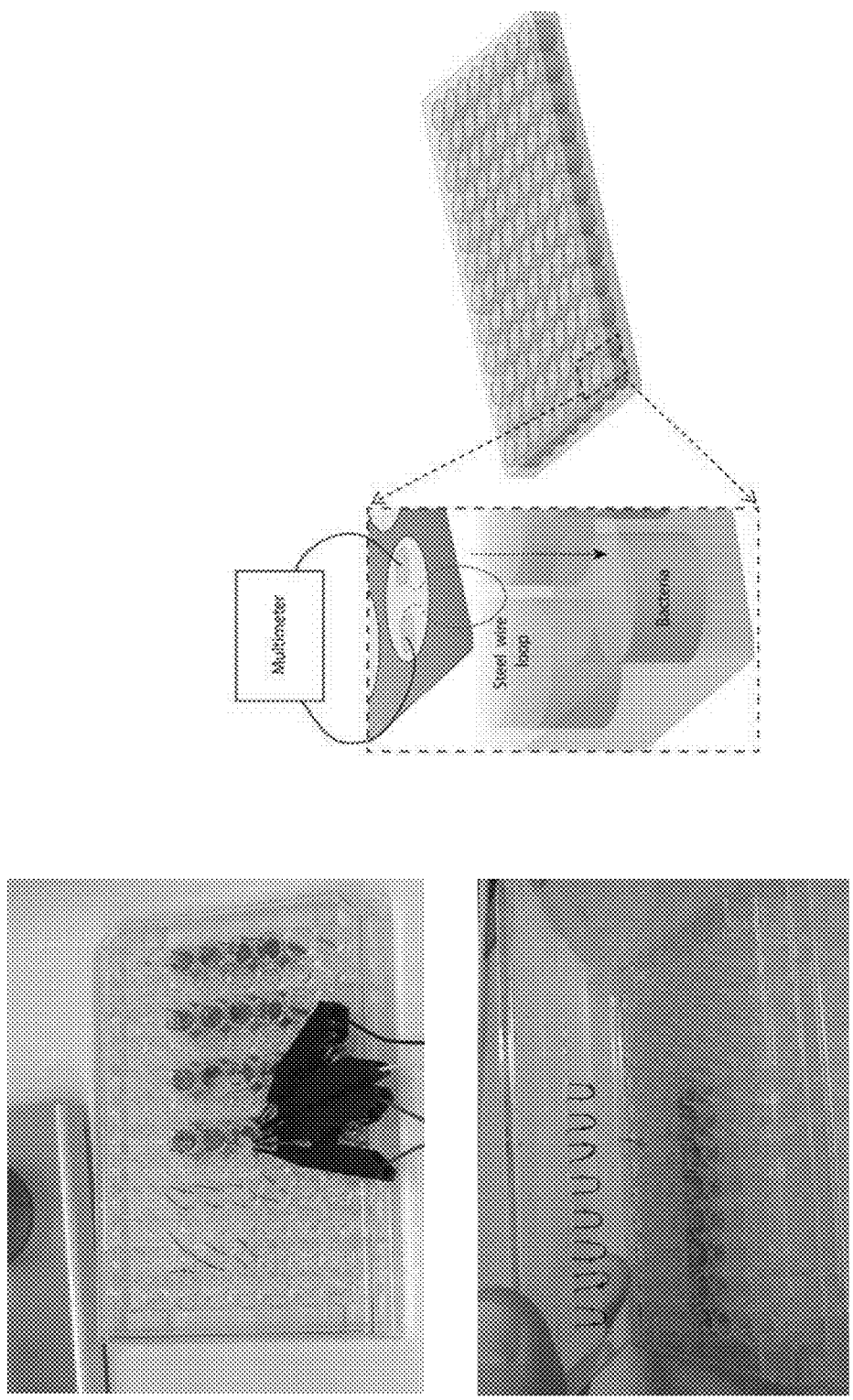
FIG. 4 is photographs and a schematic depicting one embodiment of a parallel resistance setup in a 96-well format.

Because the resistance (R) of a wire is dependent on its cross sectional area ($R=\rho L/A$ where $\rho$ is the resistivity of the metal, L is the length, and A is the cross-sectional area), the resistance of a wire will increase as corrosion reduces its cross-sectional area. Monitoring the change in resistance therefore gives an indication to the underlying corrosion progression. FIG. 4 demonstrates one method to measure the resistance of wires within a 96-well format. A u-shaped length of steel wire is inserted through the cover of the plate through two holes drilled just larger than the diameter of the wire so that two short (~0.5 cm) length lead wires protrude from the upper surface for each well. These leads are affixed and any holes around the wire filled with a small dab of adhesive. As shown in the schematic, flat leads can also be constructed on the plate cover. Each desired well is then filled with the desired media. For microbial studies, bacteria are seeded into the wells at this point. When the cover is placed on the plate, the wires dip down into the broth providing the bacteria with an exposed steel surface on which to grow. Probes from a digital multimeter contact the leads to measure the resistance of the wire. The measurement of a single well is shown in the figure but measures can be taken in parallel for all wells using either multiple probes or by constructing a switchable circuit. This method allows observation of corrosion over time for large numbers of different bacterial strains and/or conditions over time with limited use of materials and reagents. The plate can also be placed on a computer driven automated stage and the multimeter run through the computer to allow for fully automated data acquisition from each independent well.

Figure 5:
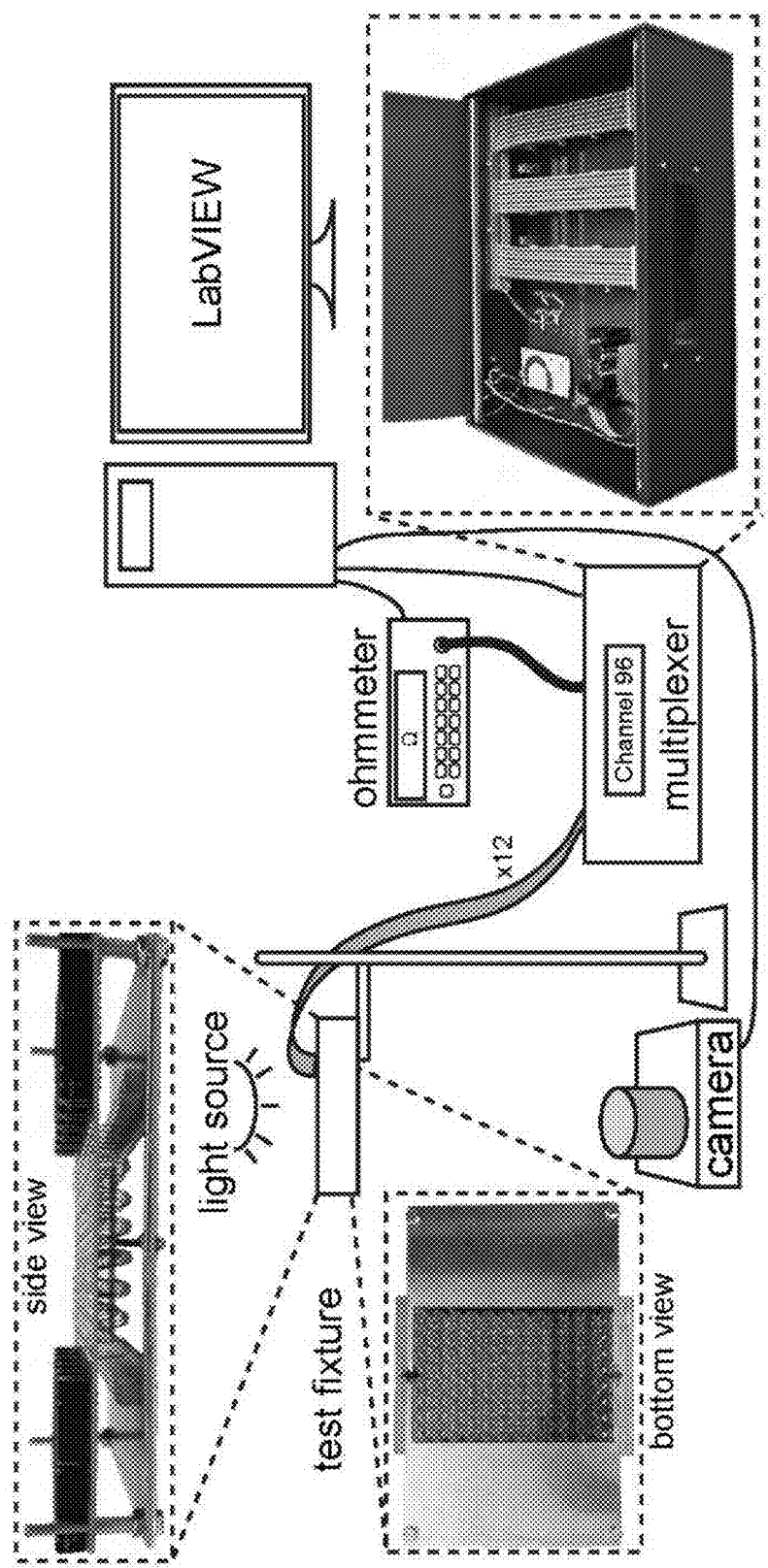
FIG. 5 is photographs and a schematic depicting another embodiment of a parallel resistance setup in a 96-well format.

In another embodiment, each u-shaped wire loop is soldered to an integrated circuit board ("test fixture") that sits on top of a 96-well plate and suspends each wire into a well (FIG. 5). This circuit board has four traces for each wire allowing 4-wire resistance measurements to be taken for each wire without manual manipulation of probes. This test fixture is connected to a multiplexer which allows a computer to control which well an ohmmeter takes a measurement from at any given time. Such a system significantly reduces measurement noise and limits the amount of experimenter input required and can enable increased sensitivity and accuracy of measurements.

The circuit board is particularly useful to find a right condition to form a good biofilm because a number of different conditions including chemical composition of surrounding medium, gas concentrations, temperature, and microbial species can be tested at the same time. For example, a biofilm increases the rate of corrosion in general, but biofilms formed by aerobic bacteria can decrease metal corrosion. However, these protective aerobic biofilms may ultimately enhance corrosion due to colonization of anaerobic pockets by SRB which cause an increase in corrosion by the removal of hydrogen and also by the production of hydrogen sulfide and iron sulfide. See, Jayaraman A. et al, Journal of Industrial Microbiology & Biotechnology (1997) 18, 396-401, which is incorporated by reference in its entirety. Therefore, finding an optimum level of biofilm requires an intricate balance of aforementioned conditions. By employing a circuit board embodiment, one can efficiently modify a corrosion condition so that an ideal biofilm with optimum thickness and morphology would be formed with minimal corrosive loss.

Other Advantages of Wire-Based Corrosion Measurements

Figure 6B:
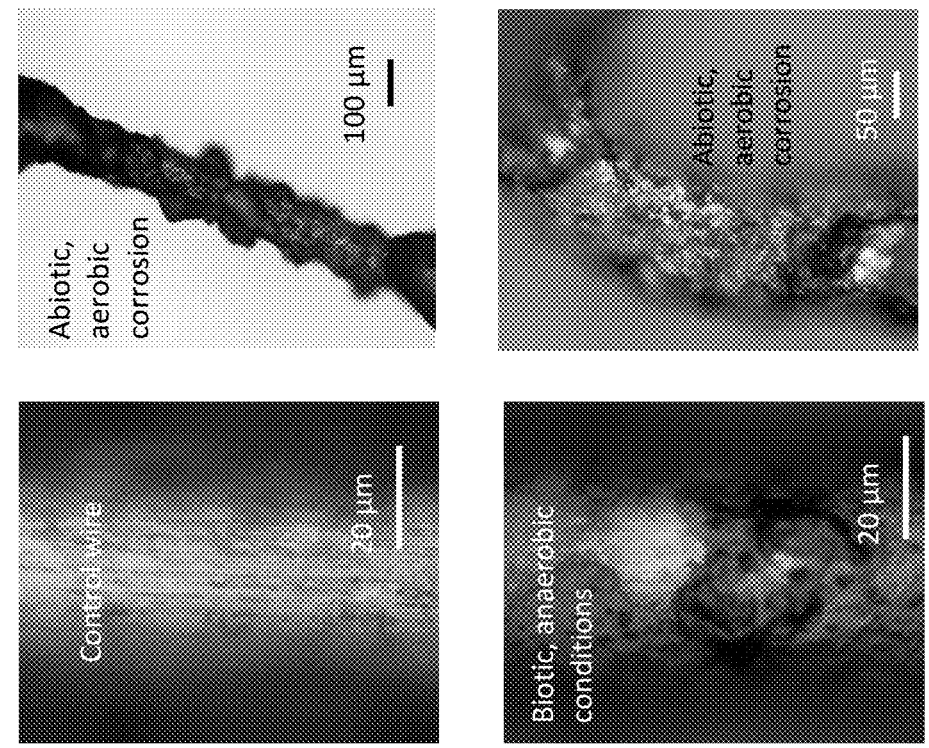
FIG. 6B is a series of images depicting easy visual assessment of corrosion process with dry wires.
Figure 6A:
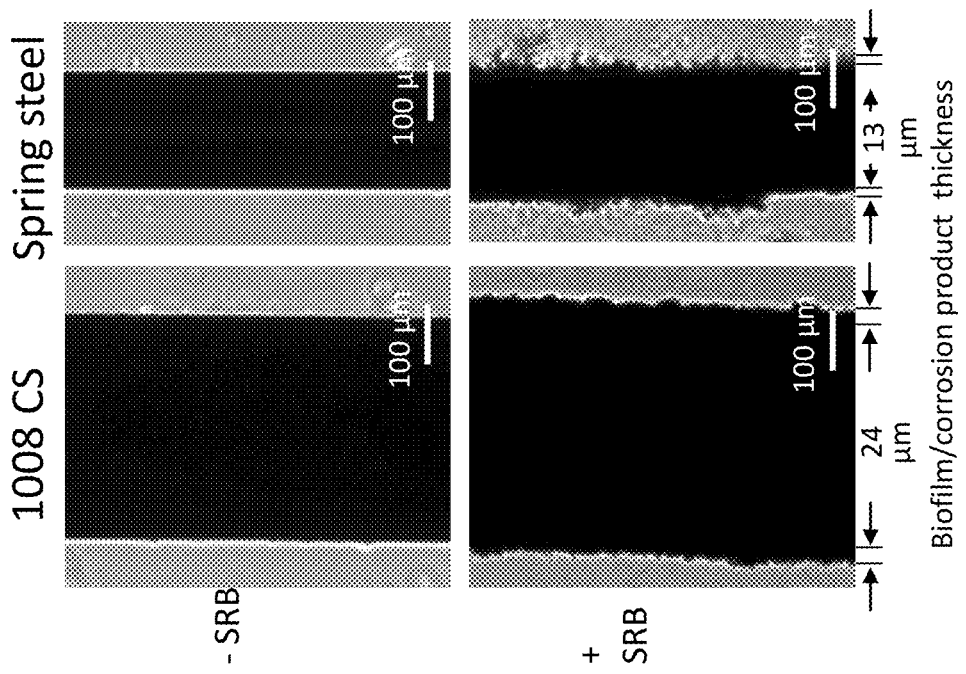
FIGS. 6A and 6C are a series of images depicting easy visual assessment of corrosion process with wires in fluid.
Figure 6C:
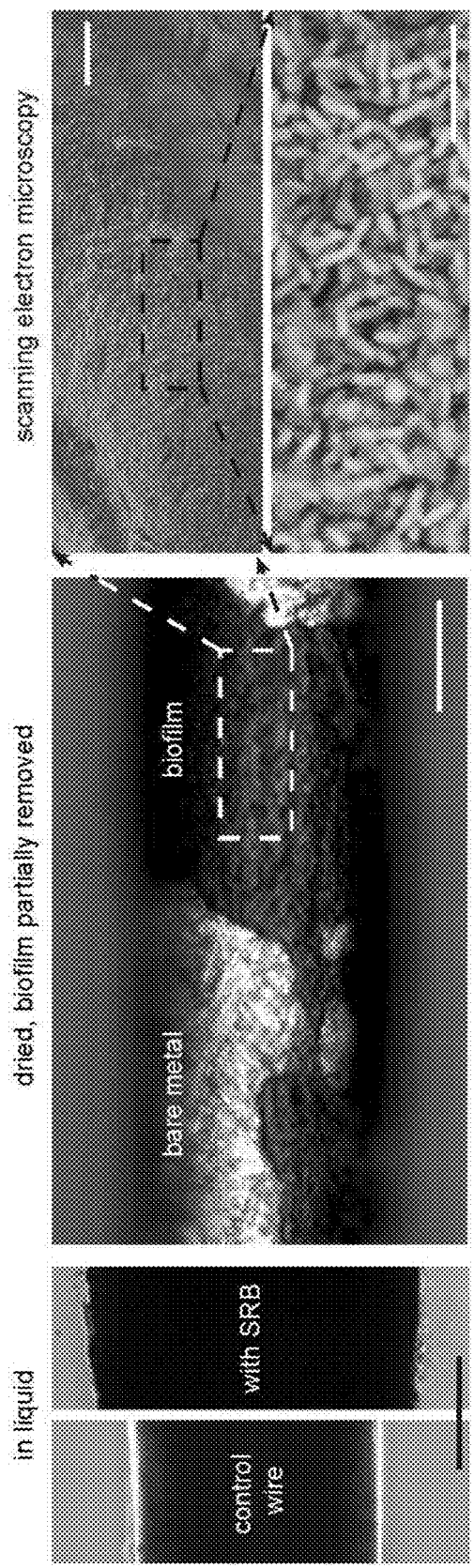

In addition to colorimetric and resistance measurements, several other properties can be easily assessed with wire-based resistance measurements. As FIG. 6 shows, the curvature of the wire provides a pseudo cross-sectional view allowing non-destructive visual assessment of the corrosion process and/or biofilm. When compared to control wires, this can reveal biofilm morphology and thickness or corrosive loss. This imaging can be performed both with wires still in fluid as in FIGS. 6A and 6C or for dried wires as in FIG. 6B.

Aerobic Corrosion

As a demonstration of the ability to track corrosion by measuring resistance over time, an aerobic corrosion experiment was performed with 1008 carbon steel wire using the more manual embodiment described above (FIG. 7). Wells were filled with either a highly corrosive solution (phosphate buffered saline (PBS)) or less corrosive DI water (FIG. 7A). A wire not exposed to any fluid was used as a control, and the resistance of the wire was measured at least daily for three weeks. As expected, the wires in PBS corroded the fastest with one wire corroding all the way through by the end of the experiment (FIG. 7B). The increase in resistance was coupled with visible corrosion products and a reduction in wire thickness (FIG. 7C). From the resistance data, several properties of the wire can be estimated such as the wire radius and cross-sectional area lost per day (FIG. 7D). The different behavior of wires in the same conditions demonstrates the need for parallel experiments to account for variability.

Figure 8:
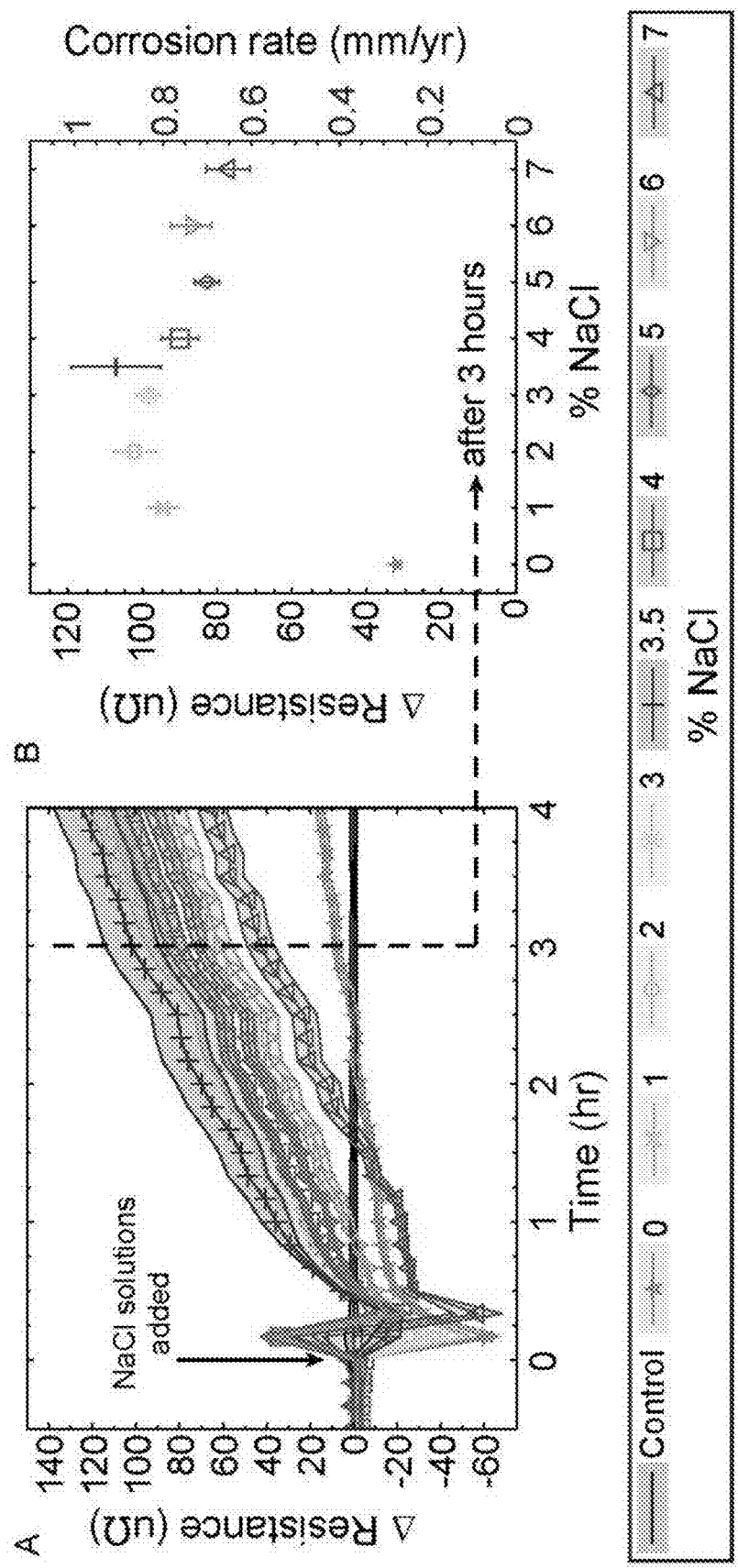
FIG. 8 shows the results of 96 independent abiotic, aerobic corrosion experiments performed in parallel.

As a demonstration of the second, highly automated high-throughput resistance measuring embodiment described above, an aerobic corrosion experiment was performed with 96 u-shaped 1008 carbon steel wires (FIG. 8). Each column of a 96-well plate served as 8 repeats of 12 different environmental conditions from control (no liquid) to 0-7% sodium chloride (w/v). Resistance changes were detectable within 1-2 hours in this embodiment, with sufficient resolution to identify distinctions in resistance among the different conditions.

Anaerobic Corrosion

Figure 9:
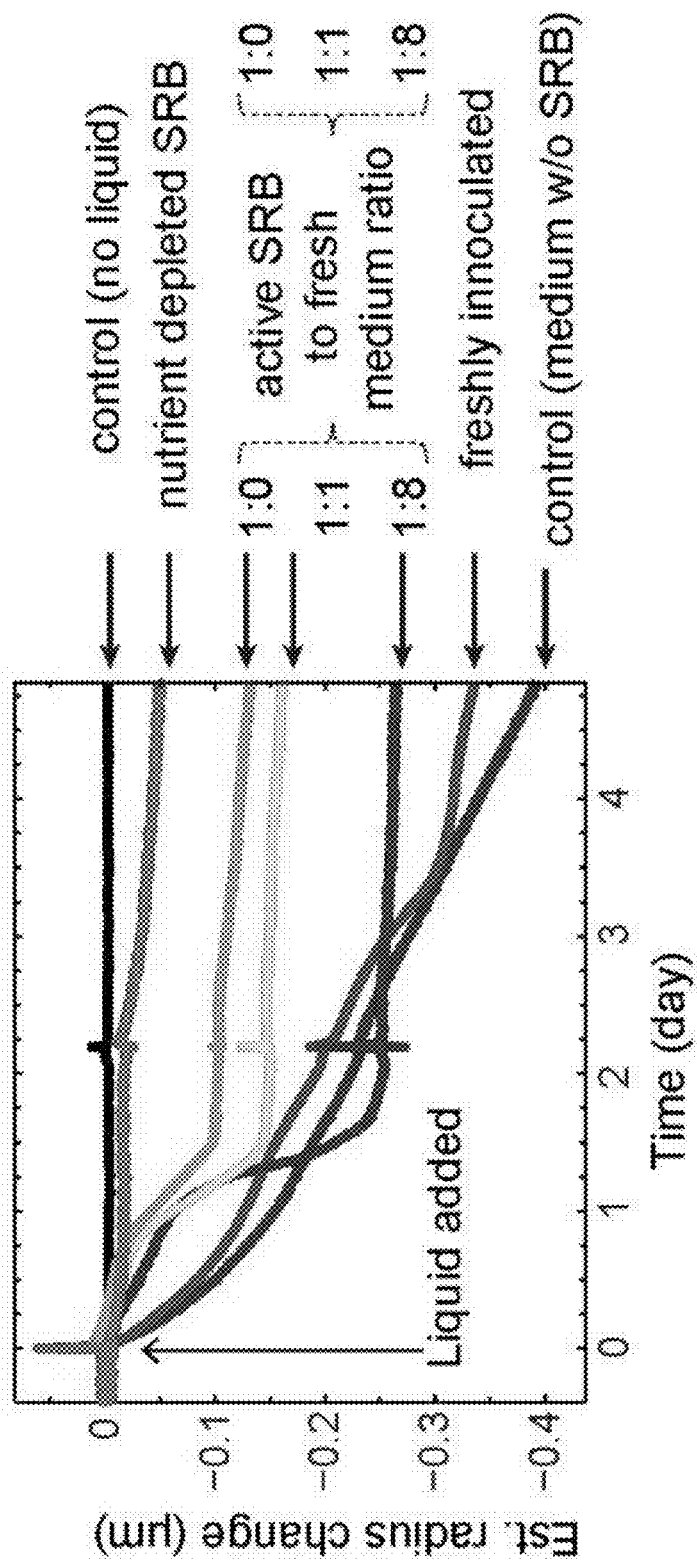
FIG. 9 is a graph depicting the change of radius of a wire as a function of time showing the results of 96 independent biotic, anaerobic corrosion experiments performed in parallel.

As a demonstration of corrosion measurements in an anaerobic environment, u-shaped wire loops were suspended within each well of a 96-well plate and placed in conditions containing SRB and varying amounts of bacterial nutrients. FIG. 9 shows the resulting radius change of the wire (as a corollary to resistance change) for the different conditions, including varied volumetric ratios of the bacteria (active SRB) to the conditioning reagent (medium).

Corrosion in Flow Conditions

Figure 10A:
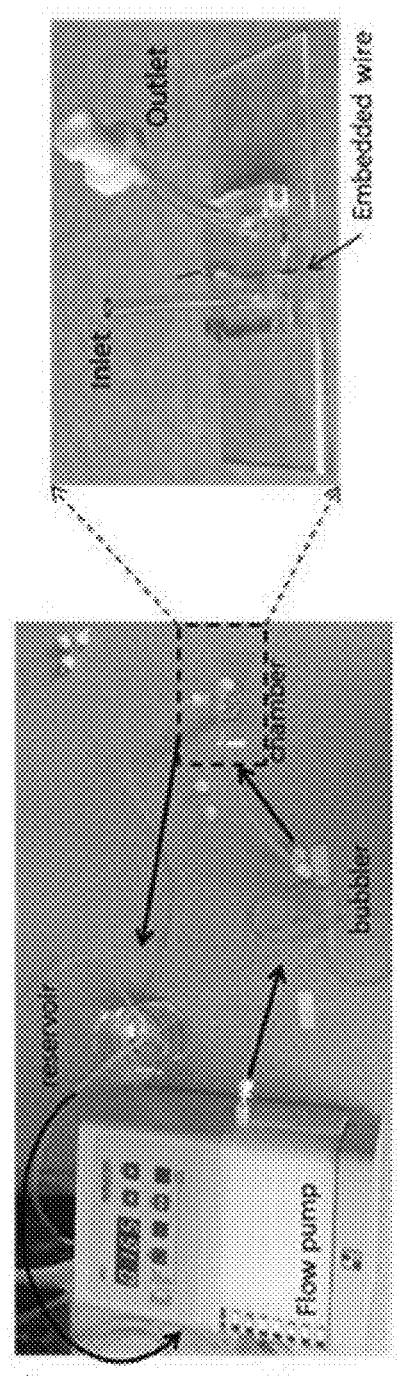
FIGS. 10A-10B are a series of photographs depicting wire-based corrosion measurements under flow.

In certain environments such as pipelines, fluid flows create shearing forces at the metal surface which can affect corrosion. The wire corrosion studies can be adapted to probe corrosion in flow conditions. FIG. 10A demonstrates an example setup for an assay with a single microchannel. To construct the wire-embedded channel, a wire is sandwiched between two spacers; each of which is half the height of the desired channel. This channel mold is placed in a lab dish and then polydimethylsiloxane (PDMS) is poured over the mold and allowed to harden. The PDMS is then peeled off of the dish and both of the spacers removed, leaving the wire spanning the channel and embedded in the PDMS walls. The ends of the wire can either be exposed by removing the PDMS from the ends or it can be bent at the ends so that they protrude out of the PDMS before pouring. The device is then sealed to a glass or other surface. A port is inserted at each end of the channel. A pump creates fluid flow through the channel and thus across the wire. The fluid can either circle back to the original reservoir to close the loop and allow continuous perfusion or separate inlet and outlet reservoirs can be used. Flow rates can be varied from across several decades.

Figure 10B:
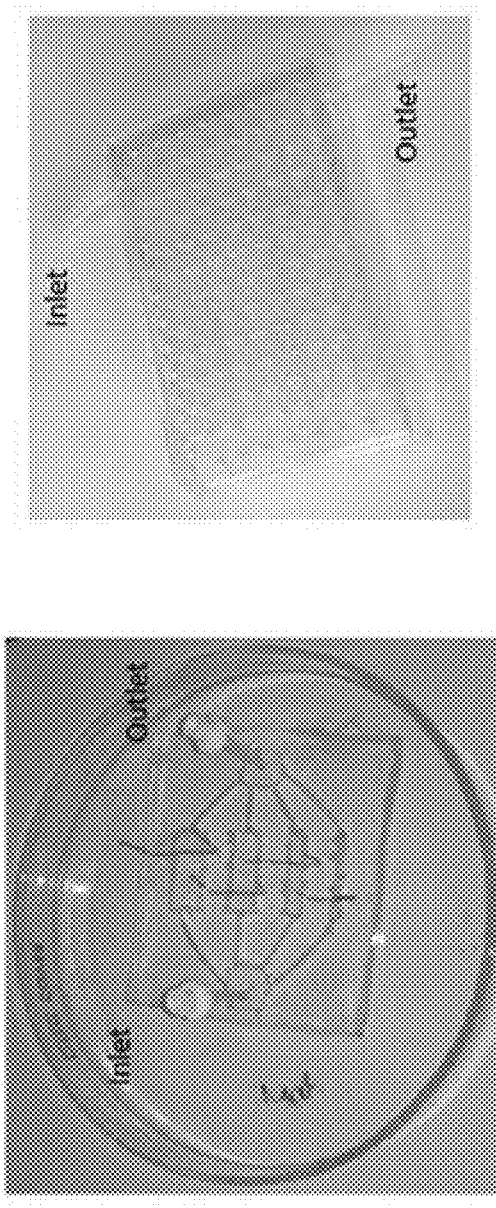

The flow studies can be performed in parallel by creating more complex microchannels within at PDMS microfluidic device, or by adapting a 96-well plate to allow flow fluid across all the channels in a column or row (FIG. 10B). A nominal pseudo-flow that serves to exchange the media can also be achieved by replacing the bottom half of the 96-well plate at desired time points.

Figure 11:
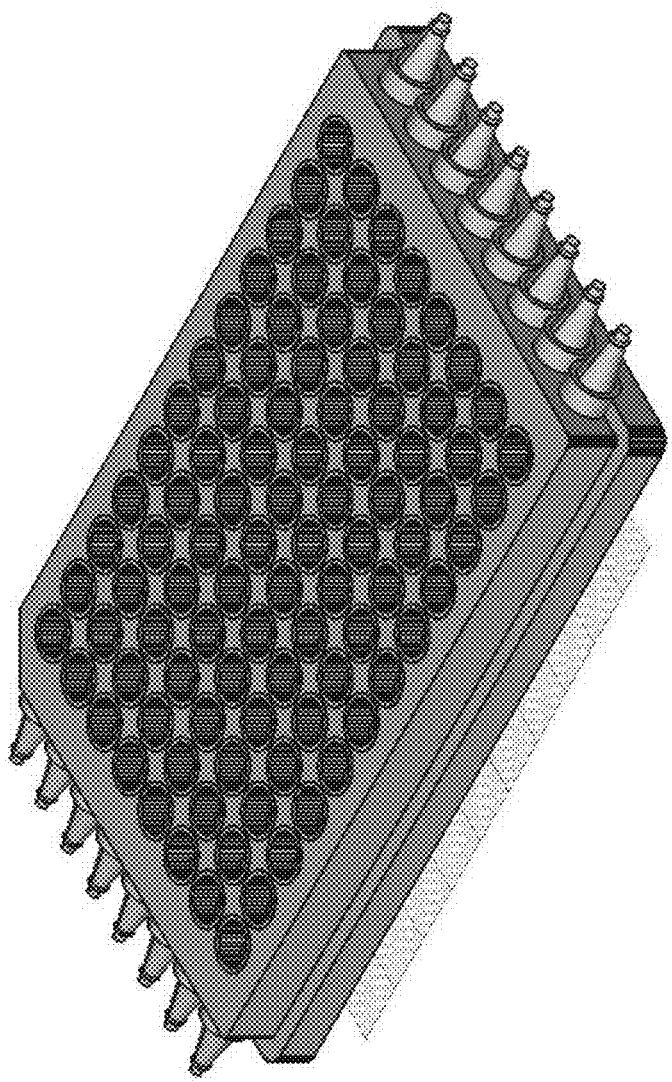
FIG. 11 is a schematic depicting an embodiment where each of the 12 wells in a row are connected forming 8 continuous channels that have an inlet/outlet port at each end of the well plate.
Figure 12:
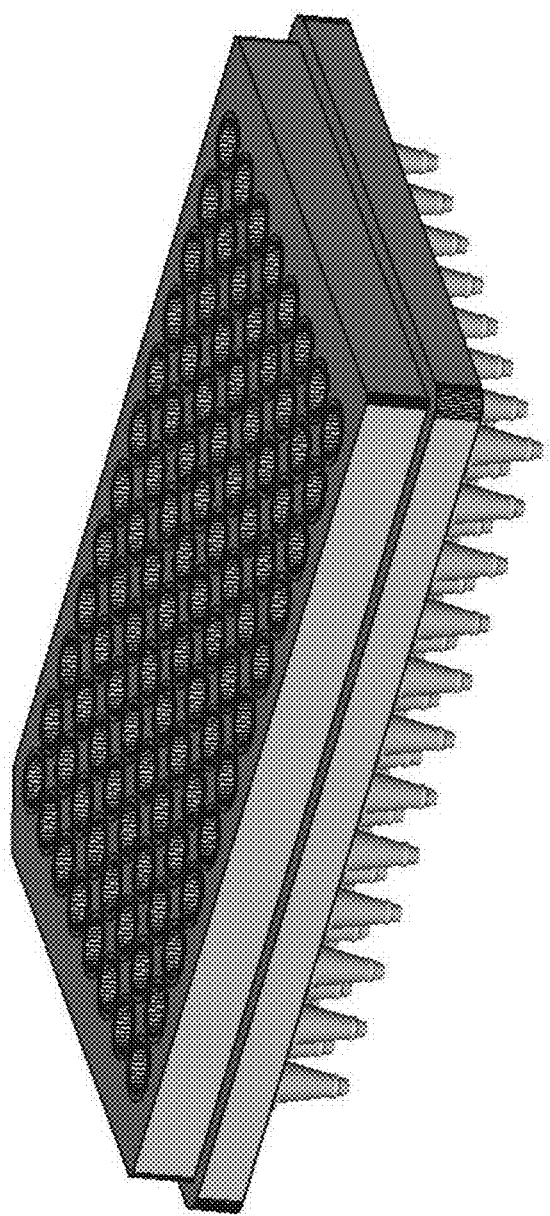
FIG. 12 is a schematic depicting an embodiment where the bottom of each well have a single or double port allowing independent control of the flow through each well.

In another embodiment, each of the 12 wells in a row can be connected forming 8 continuous channels that have an inlet/outlet port at each end of the well plate (FIG. 11). Similarly the channels can run along each column forming 12 independent flow channels. In another embodiment, the bottom of each well can have a single or double port allowing independent control of the flow through each well (FIG. 12). In this embodiment, the flow can be introduced from the top of the wells and removed through the bottom port by gravity or negative pressure or a pumping system can be used to add and remove fluids through the bottom port(s). The flow in each channel can also be independently controlled by having integrated microfluidic channels (similarly to the integrated circuit traces for the resistance measurements).

The ports can be configured to accept any tubing size. The flow rates within the wells can be the same or independently controlled using different tubing sizes or pumping rates. This can function as an open-system or have the tops of the chambers sealed. In the sealed configuration, the wires can pass through a rubber sheet that is clamped to the well plate. Alternatively, any material can be used as a top with gaskets sealing around each wire. This material can be transparent to allow imaging of the chambers. Flow can be driven by pushing or pulling the fluid through with positive or negative pressure or a combination of the two.

Other embodiments are within the scope of the following claims.

What is claimed is:

1. A method of assaying corrosion susceptibility of a sample comprising:
   providing a sample in a test cell, wherein the sample is in the form of a wire that connects two electrical contact points in the test cell, and the test cell includes an environment, a curvature of the wire providing a pseudo cross-sectional view allowing non-destructive visual assessment of corrosion:
   measuring a property of the sample or the environment in the test cell while incubating the sample in the test cell, wherein the property comprises both a visual assessment of a change of curvature of the wire and one or more of a change of color of the sample, a change of color of the environment, and a change of resistance of the sample; and
   determining the corrosion susceptibility of the sample based on the measured property.

2. The method of claim 1, wherein measuring the property occurs after incubating the sample in test cell for a defined period of time.

3. The method of claim 2, wherein the defined period of time is less than a month.

4. The method of claim 2, wherein the defined period of time is less than a week.

5. The method of claim 2, wherein the defined period of time is less than a day.

6. The method of claim 1, wherein the environment includes a plurality of microbes.

7. The method of claim 1, wherein the environment includes a solution.

8. The method of claim 7, wherein the test cell communicates with a source, wherein the source is designed to replenish the solution.

9. The method of claim 1, wherein the environment includes a gas.

10. The method of claim 9, wherein the test cell communicates with a source, wherein the source is designed to replenish the gas.

11. The method of claim 9, wherein the gas includes oxygen.

12. The method of claim 1, wherein the test cell is a confined space.

13. The method of claim 12, wherein the confined space is a microfluidic channel.

14. The method of claim 1 wherein a plurality of test cells and a plurality of samples are provided, and wherein each sample is incubated in a separate test cell.

15. The method of claim 14, further comprising measuring a property of each sample or each environment in each test cell.

16. The method of claim 14, wherein the plurality of test cells are configured in a 96 well plate format.

17. The method of claim 1, wherein measuring the property comprises measuring a change of color of the sample.

18. The method of claim 1, wherein measuring the property comprises measuring a change of color of the environment.

19. The method of claim 1, wherein measuring the property comprises measuring a change of resistance of the sample.

20. The method of claim 1, wherein measuring the property comprises measuring a change of curvature of the sample.

21. The method of claim 17, wherein the wire is in the shape of a loop.

22. The method of claim 17, wherein the sample is less than 1 cm long.

23. A system of assaying corrosion susceptibility of a sample comprising:
   a sample, wherein the sample is in the form of wire;
   a test cell to determine the corrosion susceptibility of the sample on a real-time basis, wherein the test cell includes an environment and the sample in the form of a wire connects two electrical contact points in the test cell, a curvature of the wire providing a pseudo cross-sectional view allowing non-destructive visual assessment of corrosion;
   and a means for measuring a property of the sample or the environment in the test cell on a real-time basis while the sample is incubated in the test cell, wherein the property comprises both a visual assessment of a change of curvature of the wire and one or more of a change of color of the sample, a change of color of the environment, and a change of resistance of the sample.

24. The system of claim 23, further comprising:
a plurality of samples and a plurality of test cells, wherein each sample is incubated in a separate test cell to determine the corrosion susceptibility, wherein each sample connects two electrical contact points in each test cell, and each test cell includes an environment, and wherein each sample is in the form of wire.

25. The system of claim 24, wherein each sample is incubated in a different condition.

26. The system of claim 24, wherein the plurality of test cells are configured in a 96 well plate format.

27. The system of claim 23, wherein the test cell is connected to an automated requisition device.

28. The system of claim 23, wherein the sample is less than 1 cm long.

29. The system of claim 23, wherein the environment includes a plurality of microbes.

30. The system of claim 23, wherein the environment includes a solution.

31. The system of claim 30, wherein the test cell communicates with a source, wherein the source is designed to replenish the solution.

32. The system of claim 23, wherein the environment includes a gas.

33. The system of claim 32, wherein the test cell communicates with a source, wherein the source is designed to replenish the gas.

34. The system of claim 32, wherein the gas includes oxygen.

35. The system of claim 23, wherein the test cell is a confined space.

36. The system of claim 35, wherein the confined space is a microfluidic channel.

37. The system of claim 23, wherein the wire is in the shape of a loop.

38. A method of identifying a corrosion condition of a sample comprising:
providing a plurality of test cells, wherein a sample is incubated in each test cell and each sample is in the form of a wire that connects two electrical contact points in each test cell, a curvature of each wire providing a pseudo cross-sectional view allowing non-destructive visual assessment of corrosion, and each test cell includes an environment, measuring a property of each sample or each environment in each test cell while the samples are incubated in the plurality of test cells, wherein the property comprises both a visual assessment of a change of curvature of the wires and one or more of a change of color of the samples, a change of color of the environment, and a change of resistance of the samples; and identifying an environment in one of the plurality of test cells in which a corrosive loss is reduced.

39. The method of claim 38, wherein measuring the property comprises measuring a change of color of the sample.

40. The method of claim 38, wherein measuring the property comprises measuring a change of color of the environment.

41. The method of claim 38, wherein measuring the property comprises measuring a change of resistance of the sample.

42. The method of claim 38, wherein measuring the property comprises measuring a change of curvature of the sample.

43. The method of claim 38, wherein each wire is in the shape of a loop.

44. The method of claim 38, wherein each sample is less than 1 cm long.

45. The method of claim 38, wherein each sample is soldered to an integrated circuit board.

46. The method of claim 38, wherein the plurality of test cells are configured in a 96 well plate format.

47. The method of claim 46, wherein the plurality of test cells are connected to an integrated circuit board.

48. The method of claim 47, wherein the plurality of samples are soldered to the integrated circuit board.

49. The method of claim 38, wherein each test cell is a confined space.

50. The method of claim 49, wherein the confined space is a microfluidic channel.

* * * * *